Figure 1:
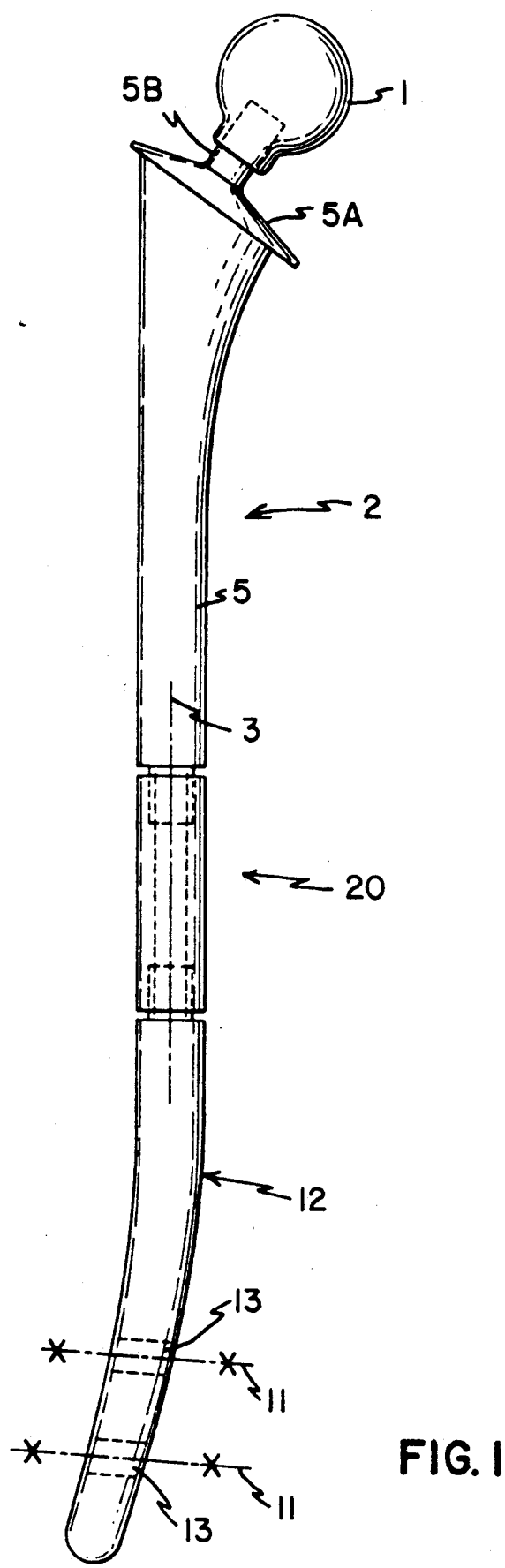

United States Patent [19]

Schelhas et al.

[11] Patent Number: 5,032,130
[45] Date of Patent: Jul. 16, 1991

[54] HIP PROSTHESIS

[75] Inventors: Klaus-Dieter Schelhas, Bremen; Hans-Michael Niedermeier, Oberwesel, both of Fed. Rep. of Germany

[73] Assignee: Bristol-Myers Squibb Company, New York, N.Y.

[21] Appl. No.: 496,358

[22] Filed: Mar. 20, 1990

[30] Foreign Application Priority Data

Mar. 21, 1989 [DE] Fed. Rep. of Germany ... 3909182[U]
Mar. 29, 1989 [DE] Fed. Rep. of Germany ....... 8903850

[51] Int. Cl.$^5$ ............................................... A61F 2/32
[52] U.S. Cl. ................................................... 623/23
[58] Field of Search ..................... 623/16, 18, 20, 22, 623/23

[56] References Cited

U.S. PATENT DOCUMENTS 4,895,572 1/1990 Chernoff ............................... 623/23

FOREIGN PATENT DOCUMENTS 0212192 7/1986 European Pat. Off. .
2605180 2/1976 Fed. Rep. of Germany .
3605630 2/1986 Fed. Rep. of Germany ........ 623/23

Primary Examiner—David J. Isabella
Attorney, Agent, or Firm—Merchant & Gould, Smith, Edell, Welter & Schmidt

[57] ABSTRACT

A thigh section having a top end carrying a ball joint element for a femoral prosthesis, including bone nails of different lengths and cross-sections which are selected upon the particular patient femur, and that can be firmly joined with the thigh section by coupling elements. The thigh section may be introduced, into the marrow space of the patient, cement-free and anchored to the bone by two transverse screws in compression/tension fashion.

7 Claims, 2 Drawing Sheets

HIP PROSTHESIS

DESCRIPTION

The invention concerns a thigh section for an acetabular prosthesis, with a shaft section whose top end carries a ball joint.

These types of thigh sections for acetabular prostheses are known in the most varied forms of embodiment and serve for replacement of the natural hip head of the thigh bone in humans. Here, serving for anchoring the thigh section is a shaft part that is inserted into the marrow space of the patient bone, without cement or with addition of bone cement, and affixed there. Since these types of thigh sections, because of the continuous, strong stressing, tend to loosen, there unfortunately continues to exist the necessity to remove loosened thigh sections by so-called exchange operations and to replace them by new thigh sections. With these types of exchange operations,—in particular in the case of brittle thigh bones -fractures can occur, in particular spiral fractures below the builtout thigh section, that extend about the entire circumference of the patient femur and considerably impair the strength of the bone and therewith the anchoring capability for the new thigh section to be installed.

In the case of exchange operations, in particular with fracture formation in the patient femur, it is known how to emplace thigh sections having a particularly long shaft that is cemented in the undamaged lower section of bone —below the spiral fracture—and thereby being anchored. Since the bone cement, when hardening, heats up strongly because of the chemical reaction, when cementing in there exists the danger that the places of fracture in the patient femur will be damaged by the heat of the bone cement and, therefore, will no longer grow together.

Additionally known, instead of emplacing thigh sections with a particularly long shaft, even in the case of a fractured patient femur, is how to emplace a thigh section with a short shaft during an exchange operation if there is not available in the particular clinic a thigh section with a long shaft, and then to "laminate" this short shaft prosthesis with an external plate lying on the outside of the patient femur, i.e. screw together the prosthesis with the different parts of the patient femur. In doing this, it has been shown that this procedure during exchange operations does not produce a stable bone/prosthesis joint, but rather much more often, already after only a few months, leads to relative movements between bone parts and prosthesis, and therewith to repeat operations.

Therefore, the object of the invention is to further develop a thigh section of the initially-mentioned type such that, in particular in the case, i.e. during an exchange operation, of a fractured patient bone, it is implantable, enables the problem-free knitting of the patient bones and produces a stable anchoring between prosthesis and bones.

In the case of the thigh section of the initially-mentioned type, this objective is met in accordance with the invention by means of a bone nail and coupling elements that are capable of being introduced into the marrow space of the patient bones for the purpose of fixing the shaft part to the bone nail.

The advantages of the invention lie particularly in the fact that bone nails of different lengths and different cross section are kept available and are selected depending upon the length and diameter of the particular patient femur, and that can be firmly joined with the thigh section by means of the coupling elements, so that there is produced in this fashion a prosthesis with an extra long shaft adapted to the patient femur. The prosthesis with the extra long shaft adapted in this manner to the data of the patient femur is then introduced, cement-free, with its free end, i.e. with the bone nail, into the marrow space of the lower portion of the patient femur and is anchored there, e.g. by means of two transverse screws in compression- and tension-stable fashion, as well as rotation- fast, to the bone, with the prosthesis lying over the coupling element being guided through the top portion of the patient femur, and with the upper and lower part of the patient femur lying one over the other in a fitting manner at the place of fracture. Achieved in this manner is an extensively initially stable anchoring of the prosthesis in the lower portion of the patient femur, and simultaneously assured is that no cement reaches the place of the break in the patient femur, so that the place of fracture, under the loading by the movements of the patient then soon setting in, can grow together. After knitting of the patient femur, the entire patient femur then again contributes to the anchoring of the prosthesis.

The shaft section of the prosthesis lying over the coupling elements can, depending upon the patient femur and/or location of fracture, etc., be a cement-free anchorable, or a cemented-in, shaft section. Then, during implantation of the prosthesis, suitable new bone cement can be added in the top part of the fractured patient femur, and/or a cement-free anchoring can support the entire prosthesis/ bone combination.

In accordance with a particularly preferred form of embodiment of the invention, the coupling elements receive a clamping sleeve that displays at its ends contrarotating internal threads. The clamping sleeve grips over the lower end of the shaft section and the top end of the bone nail and is capable of being screwed with corresponding external threads that are disposed at the lower end of the shaft section and/or at the top end of the bone nail. Particularly preferred, the lower end of the shaft section and the top end of the bone nail display sloping contact surfaces which, when tightening the clamping sleeve, run against one another and, preferably, slide on one another over a predetermined tightening path. The connection produced in this manner between the shaft section and the bone nail characterizes itself by its particular simplicity, high strength and freedom from play, in particular, when tightening the clamping sleeve; reliably prevented with engagement of the sloping contact surfaces is also a rotational play between the shaft section and bone nail.

Particularly preferred, the lower end of the shaft section and the top end of the bone nail are structured as cylindrical pins on whose face sides are formed the sloping contact surfaces. The internal diameter of the clamping sleeve is only slightly larger than the diameter of the two cylindrical pins, so that when tightening the clamping sleeve on the corresponding, contrarotating external threads, the sloping contact surfaces run up against one another and thereby press the cylindrical pins outwardly against the internal surface of the clamping sleeve, whereby the connection between bone nail and shaft section, besides the loaded screw connections, further forms a form-locking press fit inside the clamping sleeve, which is play-free and that no longer loosens even in the case of strong, long-term loading, because the screw couplings are loaded with corresponding axial forces when the sloping contact surfaces lie against one another with the corresponding counter forces.

Advantageously, the screw coupling between the shaft section and clamping sleeve has a different thread pitch than the screw coupling between bone nail and clamping sleeve; advantageously, one screw coupling is structured as a fine thread which—with appropriate tightening load—is particularly protected against loosening.

It is particularly advantageous if the bone nails can be kept available in different diameters and different lengths in order to enable a fitting of the prosthesis to the data of the patient femur during the operation. Additionally, bone nails, clamping sleeve and shaft section of the prosthesis are adapted to one another such that they fit into one another at the joint location without changing the external diameter, whereby the data inside the marrow space of the patient femur is given particular attention.

Advantageous further developments of the invention are characterized by the features of the subclaims.

Explained in more detail in the following with the aid of the drawing is an example of embodiment of the invention.

Figure 2:
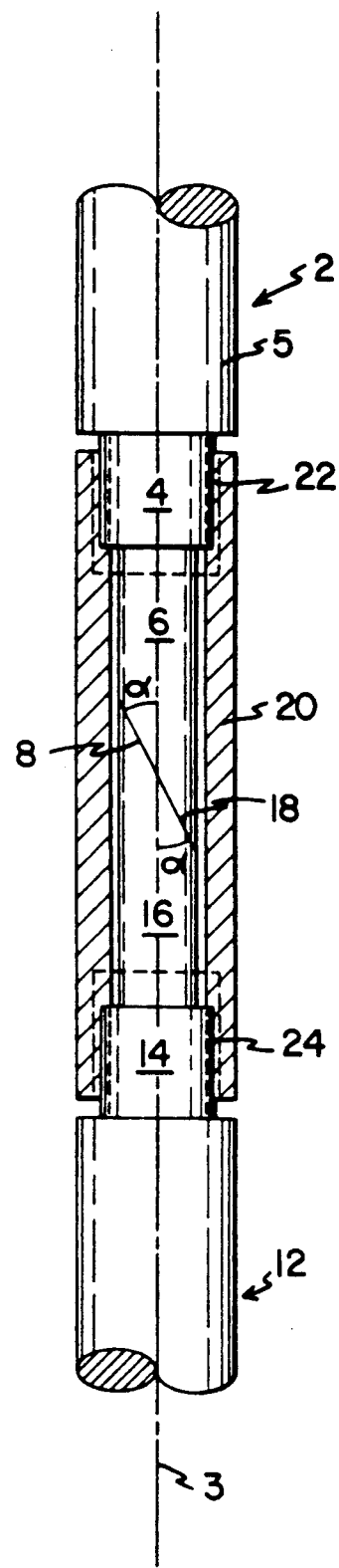

FIG. 1 shows a side view of a thigh section; and
FIG. 2 shows an enlarged cross section through the coupling location of the thigh section in accordance with FIG. 1.

FIG. 1 shows a thigh section 2 of an acetabular prosthesis that has a shaft section 5 on whose top end is formed a collar 5a and a throat 5b on which can be placed a prosthetic ball 1. Firmly joined with the shaft section 5 at the lower end of the shaft section 5 by means of a clamping sleeve 20 is a bone nail 12. The bone nail 12 is available stepped in length and diameter and is selected based on the data of the patient femur. Produced at the lower end of the bone nail 12 are two transverse borings 13 through which transverse screws 11 can be passed and that can be fastened to the patient femur.

In particular as is represented in FIG. 2, the shaft section 5 has at its lower end a cylindrical pin 6 whose end-side front face is constructed as a sloping contact surface 8. The sloping contact surface 8 is a plane that cuts the longitudinal axis 3 of the shaft section 5 at an acute angle α. The bone nail 12 is likewise constructed at its top end as a cylindrical pin 16 whose free front face is also structured as a sloping contact surface 18. The contact surface 18 is likewise flat and cuts the longitudinal axis 3 of the thigh section 2 at an angle α. At a predetermined distance from the sloping contact surfaces 8, 18, the cylindrical pins 6, 16 each carry an external thread 4, 14.

A clamping sleeve 20 surrounds the cylindrical pins 6, 16 and has at its ends contrarotating internal threads 22, 24, and can be screwed with the corresponding external threads 4, 14 of the shaft section 5 and/or of the bone nail 12 by means of the internal threads 22, 24.

The cylindrical pins 6, 16 have a length such that the sloping contact surfaces 8, 18 bear against one another and clamping sleeve 20 is screwed with the external threads 4, 14. The internal diameter of the clamping sleeve 20 is only slightly larger than the diameter of the cylindrical pins 6, 16. In the form of embodiment represented, the threads 4, 14 have, relative to the cylindrical pins 6, 16, a slightly larger diameter and relative to the then following portions of the shaft section 5 and/or of the bone nail 12, a reduced diameter. The external diameter of the clamping sleeve 20 corresponds approximately to the diameter that the shaft section 5 and the bone nail 12 have in connection with the external threads 4, 14.

The external thread of the shaft section 5 and the corresponding internal thread of the clamping sleeve 20 are structured as a fine thread. The external thread of the bone nail 12 and the associated internal thread 24 of the clamping sleeve 20 are preferably structured as normal threads.

When the clamping sleeve 20 is screwed with the shaft section 5 and the bone nail 12, the sloping contact surfaces 8, 18—with appropriate alignment—come to bear against one another and then produce a diagonal thrust. Then, if the clamping sleeve 20 is screwed further onto the external threads 4, 14, the contact surfaces 8, 18 move over one another and, in so doing, are pressed outwardly, transversely to the longitudinal axis 3, against the inner surface of the clamping sleeve 20. Additionally, when the contact surfaces 8, 18 move against one another, generated are counter forces directed in the axial direction that load the screw couplings and effectively inhibit loosening of the clamping sleeve 20, in particular in the case of the fine thread.

The relative displacement that the contact surfaces 8, 18 still cover after the contact surfaces 8, 18 have come into touching contact is designated as the tightening path. Depending upon the inclination of the sloping contact surfaces 8, 18, a relatively longer or shorter tightening path can be realized which, over several turns of the clamping sleeve 20, acts upon the screw coupling with the counter force or tightening force that holds the screw coupling under load and therewith secures against loosening.

We claim:

1. Thigh section for an acetubular prosthesis, with a shaft section (5) whose top end carries a ball joint (1), characterized by a bone nail (12) and connecting elements (6, 16, 20) capable of being introduced into the marrow space of the patient bone for fixing the shaft section (5) to the bone nail (12), the connecting elements comprising clamping sleeve (20) that displays at its ends counter-rotating internal threads (22, 24) that are capable of being screwed with corresponding external threads (4, 14) at the lower end (6) of the shaft section (5) and at the top end (16) of the bone nail (12) and sloping contact surfaces (8, 18) at the lower end (6) of the shaft section (5) and the top end of the bone nail (12), the sloping contact surfaces (8, 18) bearing against one another when the clamping sleeve (20) is tightened.

2. Thigh section according to claim 1, characterized by at least one fixing element (11) that is capable of being anchored, through an appropriate transverse boring (13) of the bone nail (12), in the patient bone.

3. Thigh section according to claim 2, characterized by the fact that the fixing element (11) is a bone screw.

4. Thigh section according to claim 1, characterized by the fact that the lower end (6) of the shaft section (5) and the top end (16) of the bone nail (12) are constructed as cylindrical pins, and that the sloping contact surfaces (8, 18) are formed on the face side of the cylindrical pins (6, 16).

5. Thigh section according to claim 4, characterized by the fact that the internal diameter of the clamping sleeve (20) is only slightly larger than the diameter of the cylindrical pins (6, 16) of the shaft section (5), respectively the bone nail (12).

6. Thigh section according to claim 1, characterized by the fact that the threads (4, 22) cooperating on the shaft section (5) have a different pitch than the threads (14, 24, cooperating on the bone nail (12).

7. Thigh section according to claim 1, characterized by the fact that the threads (4, 14) have a reduced diameter relative to the adjacent portions of the shaft section (5) and bone nail (12), respectively.

* * * * *